(12) United States Patent
Heimdal

(10) Patent No.: US 7,563,229 B2
(45) Date of Patent: Jul. 21, 2009

(54) METHOD AND APPARATUS FOR AUTOMATICALLY MEASURING DELAY OF TISSUE MOTION AND DEFORMATION

(75) Inventor: Andreas Heimdal, Oslo (NO)

(73) Assignee: GE Medical Systems Global Technology Company LLC, Waukesha, WI (US)

( * ) Notice: Subject to any disclaimer, the term of this patent is extended or adjusted under 35 U.S.C. 154(b) by 1214 days.

(21) Appl. No.: 10/459,289

(22) Filed: Jun. 11, 2003

(65) Prior Publication Data

US 2004/0254486 A1    Dec. 16, 2004

(51) Int. Cl.
*A61B 8/00* (2006.01)
(52) U.S. Cl. .................. 600/443; 600/447; 600/453; 600/454; 600/455; 600/456; 600/513; 600/587; 600/437; 600/439; 600/442; 73/573; 73/574; 73/575; 73/587
(58) Field of Classification Search .................. 600/437, 600/439, 442, 443, 447, 453–456, 513, 587; 73/573–575, 587
See application file for complete search history.

(56) References Cited

U.S. PATENT DOCUMENTS

| | | | |
|---|---|---|---|
| 5,355,887 A * | 10/1994 | Iizuka et al. ............... | 600/440 |
| 5,673,700 A * | 10/1997 | Yamazaki et al. ........... | 600/455 |
| 5,820,561 A | 10/1998 | Olstad et al. | |
| 5,970,470 A | 10/1999 | Walker et al. | |
| 6,352,507 B1 | 3/2002 | Torp et al. | |
| 6,368,277 B1 * | 4/2002 | Mao et al. .................... | 600/441 |
| 6,470,338 B1 | 10/2002 | Rizzo et al. | |
| 6,517,485 B2 | 2/2003 | Olstad et al. | |
| 6,537,221 B2 * | 3/2003 | Criton et al. ................ | 600/454 |
| 6,673,017 B1 * | 1/2004 | Jackson ...................... | 600/437 |
| 6,859,548 B2 * | 2/2005 | Yoshioka et al. ............ | 382/128 |
| 6,959,214 B2 * | 10/2005 | Pape et al. .................... | 607/17 |
| 7,231,250 B2 * | 6/2007 | Band et al. .................... | 607/18 |
| 2004/0015081 A1 * | 1/2004 | Kramer et al. .............. | 600/439 |

\* cited by examiner

*Primary Examiner*—Baisakhi Roy
(74) *Attorney, Agent, or Firm*—Dean Small; The Small Patent Law Group

(57) ABSTRACT

System and method for automatically measuring the delay of tissue motion and deformation. For example, asynchrony may be measured between the left and right ventricles and within the left ventricle. A measurement feature may be defined by default or obtained using a user input. A reference time and a search interval are identified. The search interval may be based on the reference time, or input or modified by a user. A time delay of the measurement feature within the search interval is calculated for each sample. At least one color is assigned to the samples corresponding to the calculated time delay.

20 Claims, 4 Drawing Sheets

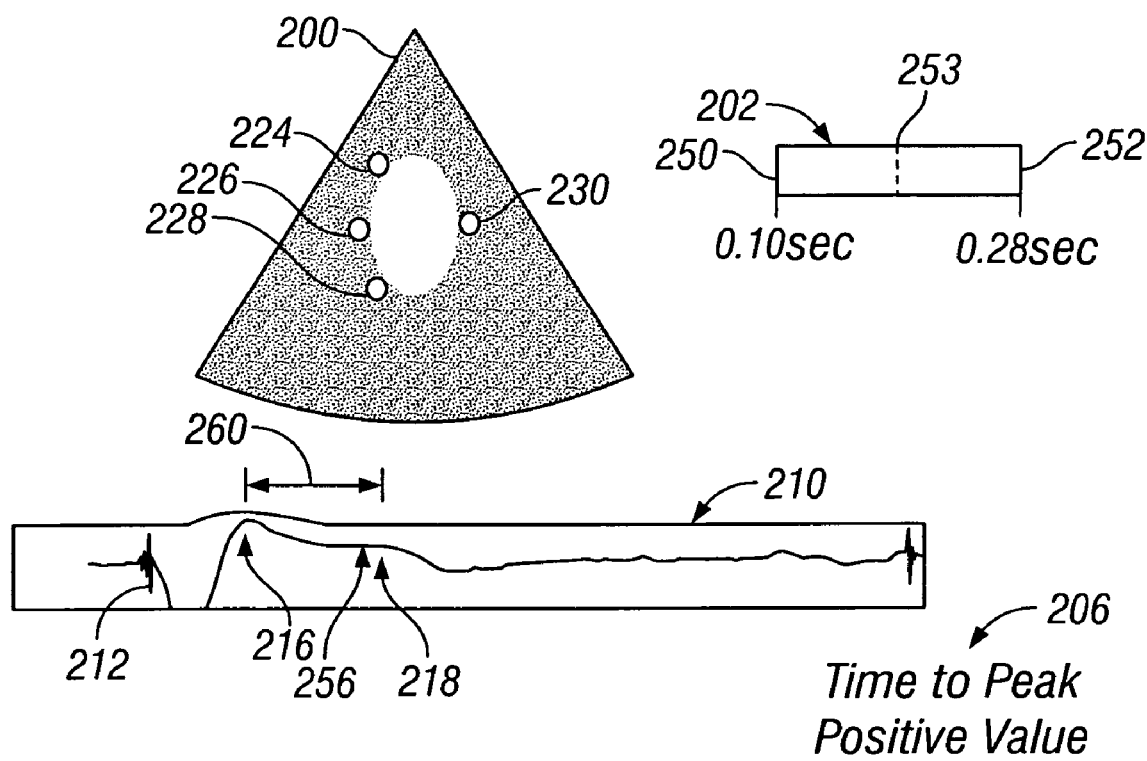
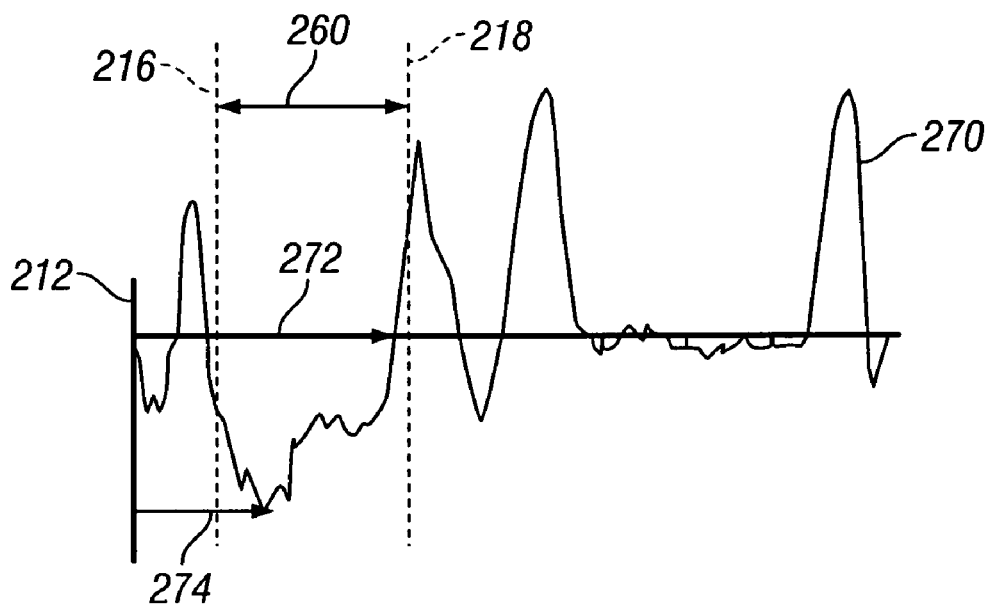
FIG. 3
FIG. 5

METHOD AND APPARATUS FOR AUTOMATICALLY MEASURING DELAY OF TISSUE MOTION AND DEFORMATION

BACKGROUND OF THE INVENTION

This invention relates generally to medical diagnostic systems. In particular, the present invention relates to method and apparatus for automatically identifying delay of cardiac tissue motion and deformation.

Patients suffering from conduction diseases may develop mechanical asynchrony, meaning that the various parts of the heart contract at different times. When the right and left ventricles do not beat with proper timing, the heart is not functioning optimally. The use of Tissue Velocity Imaging (TVI) and strain imaging to quantify the amount of synchrony between the right and left ventricle (interventricular) and within the left ventricle (intraventricular) has been suggested. One of the typical measurements is the time delay from onset of QRS to the peak in systolic velocity. Variation in this parameter between the different parts of the heart may indicate asynchrony. Other suggested parameters are the time to onset of contraction and time to onset of E-wave in velocity or strain rate.

Biventricular pacing, also known as Cardiac Resynchronization Therapy (CRT) or Ventricular Resynchronization Therapy (VRT), may help patients with asynchrony. CRT involves introducing a pacemaker with at least three leads: one in the right atrium, one in the right ventricle and one in a coronary vein of the left ventricle. The pacemaker provides an electrical signal causing the left and right ventricles to contract in synchrony, which increases the ejection fraction (EF). However, not all patients with asynchrony will benefit from this type of pacemaker.

Advanced ultrasound systems currently allow visualization of the motion and deformation of various parts of the ventricle. Unfortunately, it is not possible to automatically identify which wall, or segment of wall, is contracting earlier, and which segment(s) have delayed motion. Therefore, it is a tedious and time consuming task to manually inspect the motion or deformation pattern of each segment to assess the asynchrony.

Thus, a system and method are desired to process diagnostic data sets to easily identify the segments with delayed motion automatically, that addresses the problems noted above and others previously experienced.

BRIEF DESCRIPTION OF THE INVENTION

A method for automatically measuring the delay of tissue motion and deformation comprising obtaining a data set representative of at least one of a left and right ventricle. The data set further comprises frames of data samples from at least one heart cycle. The method further comprises obtaining a user input identifying a measurement feature. A reference time is identified within the data set, a search interval is determined within the data set, and a time delay of the measurement feature within the search interval is determined for each sample. At least one color is assigned to the samples based on the determined time delay.

A method for automatically measuring asynchrony comprising obtaining a data set representative of a left ventricle, the data set further comprising at least one heart cycle. The method includes identifying a search interval for each heart cycle based on at least one automatically detected feature, and identifying a measurement feature within the search interval. A time delay of the measurement feature within the search interval is calculated with respect to a reference time for each sample in the data set. A color is assigned to the samples based on the time delay.

A system for measuring time delay in moving or deforming tissue, comprising a transmitter transmitting ultrasound signals into an area of interest, a receiver for receiving echo signals from transmitted ultrasound signals, and a memory for storing a series of image frames comprising the echo signals. The series of image frames comprises at least one heart cycle and data samples. The system comprises a first user input for inputting a measurement feature. A signal processor identifies a search interval comprising image frames, identifies the measurement feature within the search interval, and identifies time delays of the samples within the search interval. The time delays are measured with respect to the measurement feature, and a color is assigned to each sample based on the time delays. A display displays the samples color-coded according to the time delays.

BRIEF DESCRIPTION OF THE DRAWINGS

FIG. 3 illustrates ultrasound data indicating tissue motion delay which may be displayed on the display system in accordance with an embodiment of the present invention.

FIG. 5 illustrates a map of one sample over time with two measurement functions indicated in accordance with an embodiment of the present invention.

DETAILED DESCRIPTION OF THE INVENTION

Figure 1:
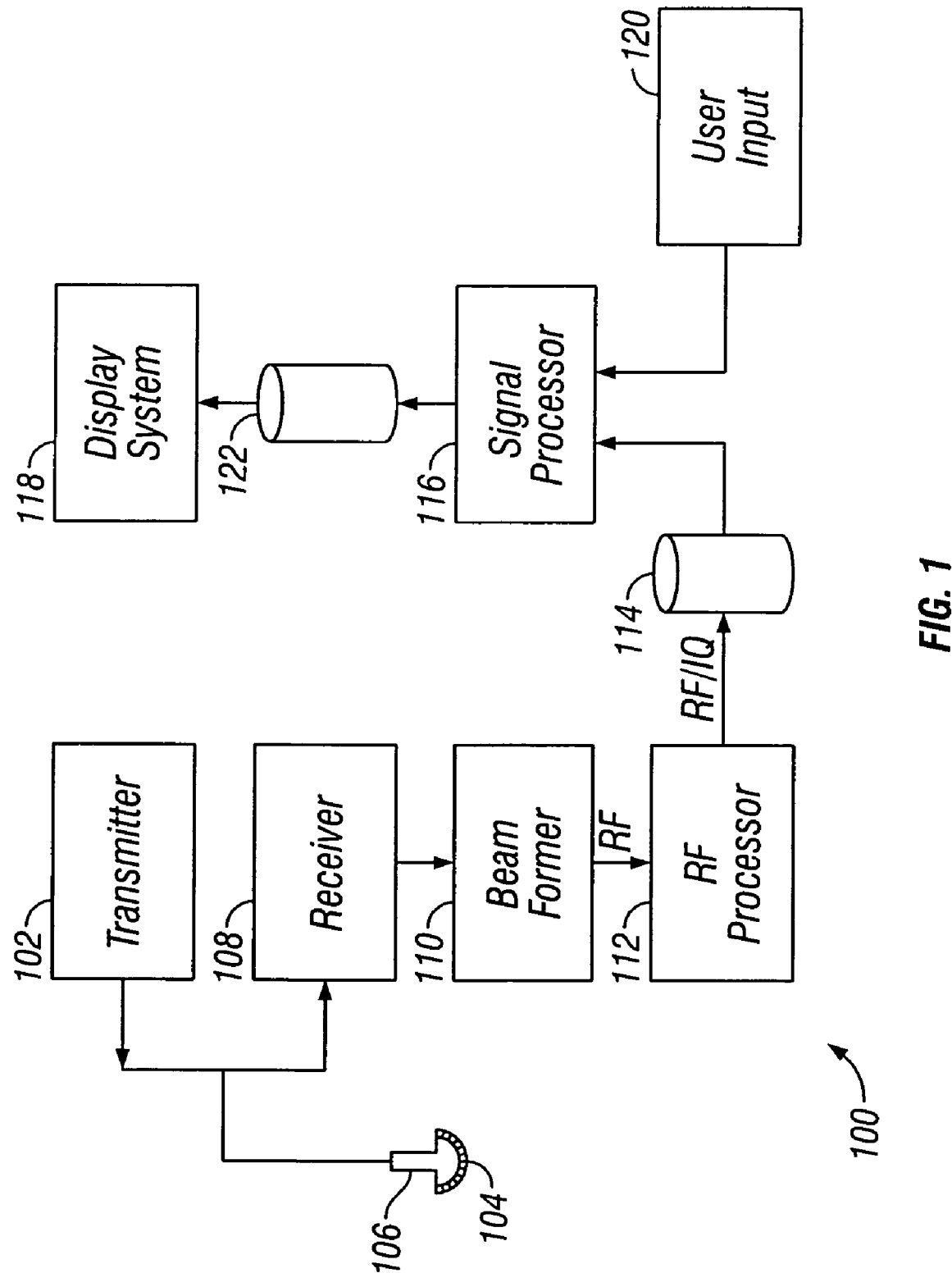
FIG. 1 illustrates a block diagram of an ultrasound system formed in accordance with an embodiment of the present invention.

FIG. 1 illustrates a block diagram of an ultrasound system 100 formed in accordance with an embodiment of the present invention. The ultrasound system 100 includes a transmitter 102 which drives transducers 104 within a probe 106 to emit pulsed ultrasonic signals into a body. A variety of geometries may be used. The ultrasonic signals are back-scattered from structures in the body, like blood cells or muscular tissue, to produce echoes which return to the transducers 104. The echoes are received by a receiver 108. The received echoes are passed through a beamformer 110, which performs beamforming and outputs an RF signal. The RF signal then passes through an RF processor 112. Alternatively, the RF processor 112 may include a complex demodulator (not shown) that demodulates the RF signal to form IQ data pairs representative of the echo signals. The RF or IQ signal data may then be routed directly to RF/IQ buffer 114 for temporary storage. A user input 120 may be used to input patient data, scan parameters, a change of scan mode, and the like.

The ultrasound system 100 also includes a signal processor 116 to process the acquired ultrasound information (i.e., RF signal data or IQ data pairs) and prepare frames of ultrasound information for display on display system 118. The signal processor 116 is adapted to perform one or more processing operations according to a plurality of selectable ultrasound modalities on the acquired ultrasound information. Acquired ultrasound information may be processed in real-time during a scanning session as the echo signals are received. Additionally or alternatively, the ultrasound information may be stored temporarily in RF/IQ buffer 114 during a scanning session and processed in less than real-time in a live or off-line operation.

The ultrasound system 100 may continuously acquire ultrasound information at a frame rate that exceeds 50 frames per second—the approximate perception rate of the human eye. The acquired ultrasound information is displayed on the display system 118 at a slower frame-rate. An image buffer 122 is included for storing processed frames of acquired ultrasound information that are not scheduled to be displayed immediately. The image frames may be stored as data sets. Preferably, the image buffer 122 is of sufficient capacity to store at least several seconds worth of frames of ultrasound information. The frames of ultrasound information are stored in a manner to facilitate retrieval thereof according to its order or time of acquisition. The image buffer 122 may comprise any known data storage medium.

Figure 2:
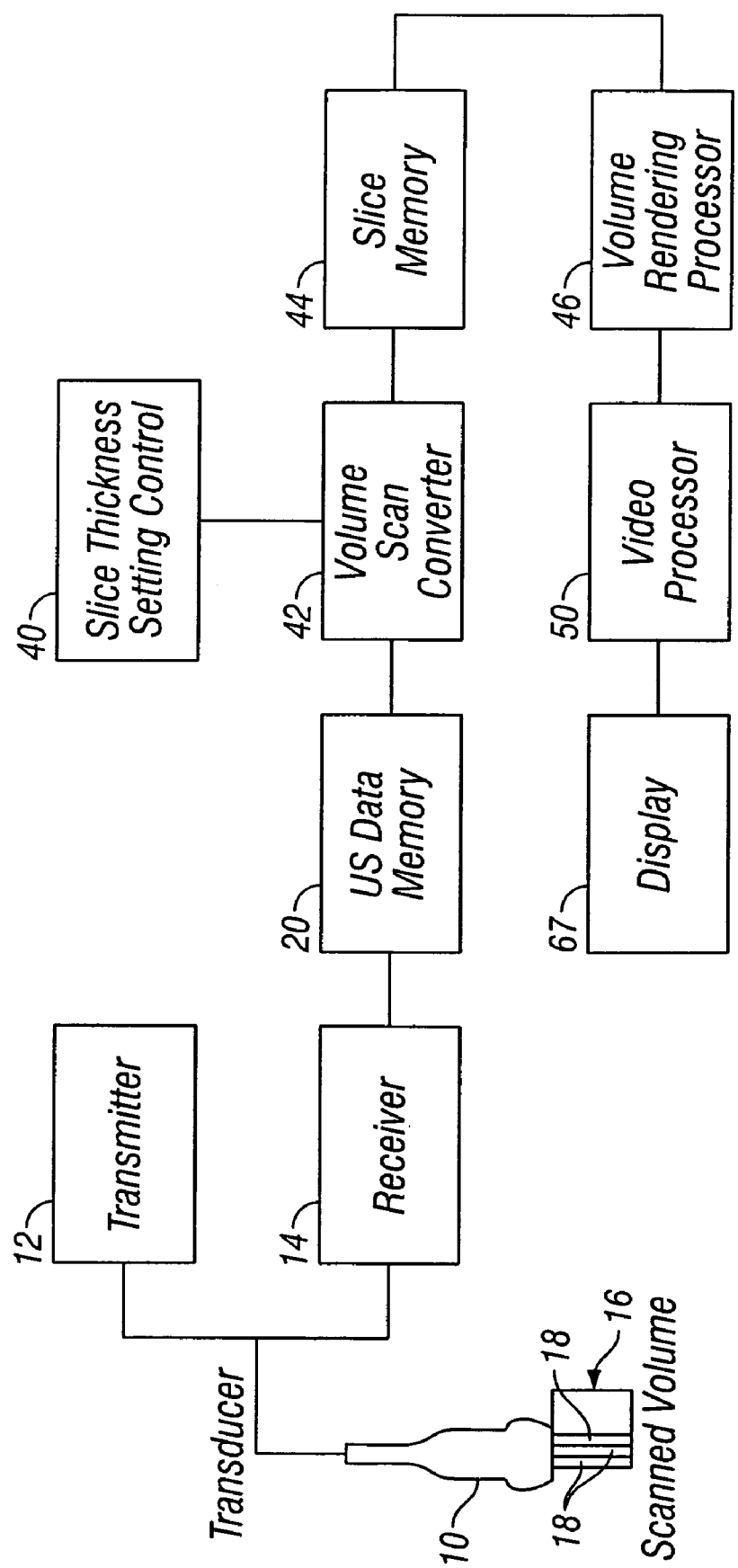
FIG. 2 illustrates an ultrasound system formed in accordance with an embodiment of the present invention.

FIG. 2 illustrates an ultrasound system formed in accordance with one embodiment of the present invention. The system includes a probe 10 connected to a transmitter 12 and a receiver 14. The probe 10 transmits ultrasonic pulses and receives echoes from structures inside of a scanned ultrasound volume 16. Memory 20 stores ultrasound data from the receiver 14 derived from the scanned ultrasound volume 16. The volume 16 may be obtained by various techniques (e.g., 3D scanning, real-time 3D imaging, volume scanning, 2D scanning with transducers having positioning sensors, freehand scanning using a Voxel correlation technique, 2D or matrix array transducers and the like).

The transducer 10 is moved, such as along a linear or arcuate path, while scanning a region of interest (ROI). At each linear or arcuate position, the transducer 10 obtains scan planes 18. Alternatively, a matrix array transducer with electronic beam steering may be used to obtain the scan planes 18 without moving the transducer 10. The scan planes 18 are collected for a thickness, such as from a group or set of adjacent scan planes 18. The scan planes 18 are stored in the memory 20, and then passed to a volume scan converter 42. In some embodiments, the transducer 10 may obtain lines instead of the scan planes 18, and the memory 20 may store lines obtained by the transducer 10 rather than the scan planes 18. The volume scan converter 20 may store lines obtained by the transducer 10 rather than the scan planes 18. The volume scan converter 42 receives a slice thickness setting from a control input 40, which identifies the thickness of a slice to be created from the scan planes 18. The volume scan converter 42 creates a data slice from multiple adjacent scan planes 18. The number of adjacent scan planes 18 that are obtained to form each data slice is dependent upon the thickness selected by slice thickness control input 40. The data slice is stored in slice memory 44 and is accessed by a volume rendering processor 46. The volume rendering processor 46 performs volume rendering upon the data slice. The output of the volume rendering processor 46 is passed to the video processor 50 and display 67.

The position of each echo signal sample (voxel) is defined in terms of geometrical accuracy (i.e., the distance from one voxel to the next) and ultrasonic response (and derived values from the ultrasonic response). Suitable ultrasonic responses include gray scale values, color flow values, and angio or power Doppler information.

Figure 4:
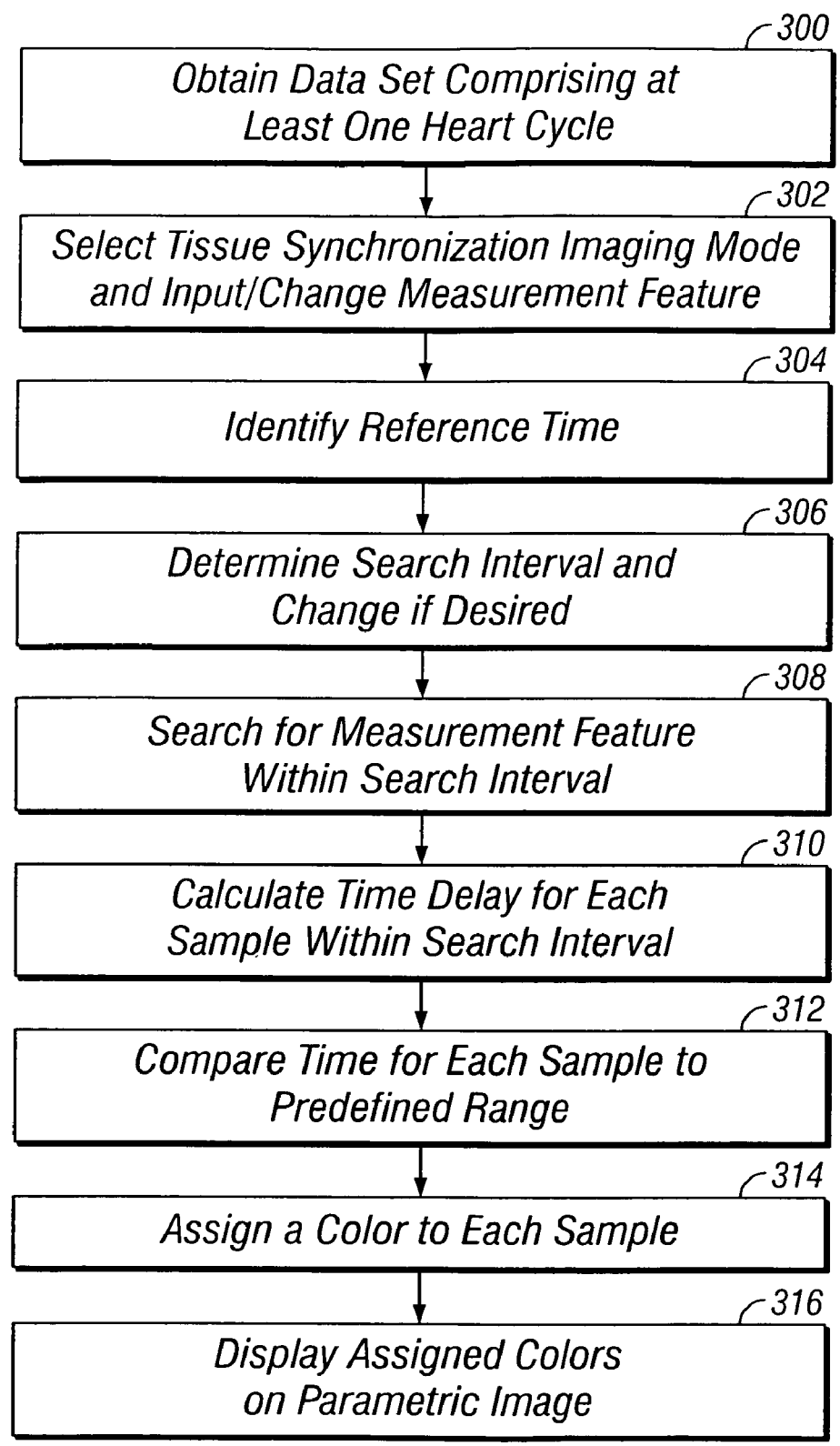
FIG. 4 illustrates a method for automatically measuring the delay of cardiac tissue, or for measuring the synchronization of tissue, in accordance with an embodiment of the present invention.

FIG. 3 illustrates ultrasound data indicating tissue motion delay which may be displayed on the display system 118. FIG. 4 illustrates a method for automatically measuring the delay of cardiac tissue motion, or for measuring the synchronization of tissue. Additionally, the method of FIG. 4 may be used to measure the motion of other tissues, such as blood vessel walls, skeletal muscles, the stomach, and the like. FIGS. 3 and 4 will be discussed together.

In step 300 of FIG. 4, the ultrasound system 100 acquires a data set of image frames comprising at least one heart cycle. The data set includes sample data which may be used to detect certain features of the motion or deformation pattern. The data set may include data representative of a left and/or right ventricle, and may be acquired in TVI mode. Alternatively, SRI, strain or tissue tracking modes may be used. It should be understood that the method of FIG. 4 may be used to process stored image frames of data, such as data stored in a cineloop. Alternatively, the method may process data in real-time, then store the processed data.

In FIG. 3, a sector image 200 may be displayed in color during a portion of the heart cycle. A color scale 202 with endpoints 250 and 252 indicates the range of colors that may be displayed on the sector image 200. Regions of interest 224-230 may be selected by the user similar to methods used in TVI imaging, strain, strain rate, and the like, or automatically identified by the ultrasound system 100. In FIG. 3, the sector image 200 illustrates the left ventricle and the regions of interest 224-230 indicate heart segments.

In step 302, a user selects tissue synchronization imaging mode using the user input 120. The user input 120 may be a rotary or slider input, a touch screen, or a soft key. The ultrasound system 100 may have a default measurement feature associated with the imaging mode being used when tissue synchronization imaging is selected. For example, when scanning using TVI, the default measurement feature may be Time to Peak Positive Value. When scanning using other modes, like strain rate, strain or Tissue Tracking, the default measurement feature may be different than the default measurement feature of TVI.

Alternatively, the measurement feature may be input or changed using the user input 120. The user input 120 may be a rotary or slider input, a touch screen, or a soft key. The user selects the measurement feature from a list of available features, such as Time to Peak Positive Value, Time to Peak Negative Value, Time to Peak Absolute Value, Time to Steepest Negative-To-Positive Crossing of a Threshold Value, Time to Steepest Positive-To-Negative Crossing of a Threshold Value, and Time to Steepest Crossing of a Threshold Value. It should be understood that other measurement features may be used.

The current measurement feature is displayed on the display system 118, as shown in text line 206 on FIG. 3. Similarly, if the data set is recorded on an external recorder, such as a VCR, optical or compact disk, or other storage medium, the selected measurement feature will be recorded and displayed when the data set is retrieved for viewing. If the user selects a different measurement feature while scanning, the text line 206 is changed to reflect the new (or current) measurement feature. It should be understood that the text line 206 may be displayed anywhere on the display system 118, and thus is not limited to the illustration of FIG. 3.

In step 304, the signal processor 116 identifies a reference time 212 within the data set. For example, the reference time 212 may be the time of onset of the QRS complex in a co-registered ECG signal.

In step 306, the signal processor 116 determines a search interval 260 comprising a portion of the heart cycle. The search interval 260 defines the window of time, and thus the image frames of the data set, which will be used to calculate the time delay of the samples. The search interval 260 has a start search time 216 and an end search time 218. The signal processor 116 indicates the start and end search times 216 and 218 on the ECG trace 210. In FIG. 3, the search interval 260 is illustrated above the ECG trace 210. The start and end search times 216 and 218 may be illustrated in any clear manner, such as by a brackets, circles, squares, Xes, or asterisks, for example.

The search interval 260 may be based on the QRS (start of systole). For example, the signal processor 116 may set default start and end search times 216 and 218 automatically at estimated times for start ejection (X ms after onset of QRS) and aortic valve closure (X % of the interval between one QRS and the next QRS, or X % of RR-interval), respectively.

The user may change the default start and end search times 216 and 218 through the user input 120. The user input 120 may be a rotary or slider input, or a mouse function allowing drag and drop, for example. The start search time 216 and end search time 218 may be moved on the ECG trace 210 and the search interval 260 is updated accordingly. The user may choose to create a smaller or larger search interval 260, or adjust one or both of the start and end search times 216 and 218 to include a desired portion of the heart cycle. Optionally, the signal processor 116 may not set default start and end search times 216 and 218, but may prompt the user to input the start and end search times 216 and 218 defining the search interval 260 by using the user input 120.

In addition, the start and end search times 216 and 218 define the color scale 202 endpoints 250 and 252. For example, the color scale 202 may range from green at end point 250, to yellow at center point 253, to red at end point 252. The numbers below endpoints 250 and 252 indicate start and end search times, 216 and 218, respectively, measured from the previous QRS. As the user modifies the start and end search times 216 and 218, the numbers change correspondingly.

In step 308, the signal processor 116 searches for the measurement feature within the search interval 260. The signal processor 116 may look at every sample in the image frames within the search interval 260 to find the time that corresponds to the measurement feature. For example, the measurement feature for Time to Peak Positive Value may be the peak positive value.

In step 310, the signal processor calculates the time delay from the reference time 212 to the measurement feature for every sample within the search interval 260. Therefore, if the data set comprises a series of image frames, only the samples of the image frames occurring between the start and end search times 216 and 218 are processed. By way of example only, the calculated time for each sample is stored in the image buffer 122 or other storage medium in a table or vector format.

FIG. 5 illustrates a graph 270 of one sample over time. Two measurement functions, the reference time 212, and the search interval 260 having start and end search times 216 and 218 are also illustrated. The graph 270 illustrates sample data, over time, for a single sample received from Strain Rate scanning, although other modes may be used. Arrow 272 illustrates the time from the reference time 212 to the Time to Zero Crossing measurement feature. Arrow 274 illustrates the time from the reference time 212 to the Time to Peak measurement feature. The signal processor 116 calculates the time delay of the measurement feature for the sample illustrated by graph 270 within the search interval 260. The signal processor repeats this calculation for every sample within the search interval 260.

Optionally, in step 312, the signal processor 116 compares the calculated time for each sample to a predefined range. The predefined range is based on the measurement feature, and identifies a normal range of delay for the tissue selected. If a sample is not within the predefined range, the sample indicates tissue delay. Each measurement feature may have a different predefined range. Therefore, Time to Peak Positive Value has a different predefined range than Time to Peak Negative Value, for example. The signal processor 116 may also identify a degree of time delay. As in step 310, the signal processor 116 may store the difference between the calculated time for each sample and the predefined range, or the identified degree of time delay, in the image buffer 122 or other storage medium in a table or vector format.

In step 314, the signal processor 116 assigns a color to each sample processed in step 310. Color is used to indicate the degree of time delay. The color assigned to each sample is based on the color scale 202 and search interval 260. For example, a sample having a short time delay is assigned a green color, a sample having a medium time delay is assigned a yellow color, and a sample having a high time delay is assigned a red color. Therefore, green indicates that the measurement feature was detected in the early part of the search interval 260, and red indicates that the measurement feature was detected in the late part of the search interval 260.

If, in step 308-310, the specified feature was not detected, the corresponding samples may be left uncolored. An example of this is if the measurement feature is Time To Peak Positive Value and only negative values were within the search interval, the corresponding samples may be left uncolored. Optionally, the user may choose to mask a portion, or subset, of time with the search interval 260. The user defines the subset of the search interval 260, and the samples within the subset are assigned a separate color not on the color scale 202, such as blue.

In step 316, the signal processor 116 displays the samples within sector image 200 in their assigned color on the display system 118. The colorized sector image 200 may also be referred to as a 2D parametric image. If regions of interest 224-230 have been selected, the samples within the regions of interest 224-230 may be averaged and the corresponding color used to display the circle defining each region of interest 224-230.

When the image data is displayed over time, either by recalling image frames previously stored in a cine-loop, or by processing data in real-time, an indicator line 256 identifying the current location within the heart cycle moves across the ECG trace 210. In FIG. 3, the indicator line 256 is within the time interval 260, and thus the image frame being displayed is also within the time interval 260. The samples are displayed in color on the parametric image when the image frame being displayed is within the time interval 260. When the indicator line 256 is outside the time interval, the image frames being displayed have not been processed for the selected measurement feature. Therefore, the parametric image may be displayed in black and white.

The tissue delay of multiple samples may be compared to identify a degree of delay. For example, samples corresponding to segments within the left ventricle may be compared to identify the most delayed segment. Similarly, segments may be compared between the left and right ventricles. Although FIG. 3 illustrates data representative of a left ventricle, thus quantifying the amount of synchrony within the left ventricle, it should be understood that the method of FIG. 4 may be used to quantify and compare the time delay of samples in the left and right ventricles to determine the amount of synchrony between the left and right ventricles. In addition, the method of FIG. 4 may be used to quantify and compare the time delay of samples in the left and right atria of the heart.

The system and method described herein include automatic detection of peaks, zero-crossings or other features of tissue velocity, displacement, strain rate and strain data as a function of time. By processing only the image frames within the selected search interval, the processing time is shortened and the possibility of false positives is lowered, such as may occur when an incorrect peak is identified. Previous methods required a user to use a measurement tool, such as a caliper, to measure the time to the selected peak or measurement feature, which required more time and skill on the part of the user and had a greater margin for error. The system and method color codes the delay of samples in the image in relation to the onset of the QRS, and presents the data as a parametric image, both in live display and in replay. Thus, heart segments or other selected tissue with delayed motion might be more easily visualized than with other imaging modes. Therefore, patients who will respond favorable to CRT may be more easily selected, and the optimal position for the left ventricle pacing lead may be located by identifying the most delayed site within the left ventricle. Furthermore, the effect of the various pacemaker settings, such as AV-delay and VV-delay, may be studied to find the optimal settings.

While the invention has been described in terms of various specific embodiments, those skilled in the art will recognize that the invention can be practiced with modification within the spirit and scope of the claims.

What is claimed is:

1. A method for automatically measuring, in an ultrasound system, synchronization of tissue motion and deformation, comprising:
    obtaining, from the ultrasound system, a data set of ultrasound samples representative of at least one of a left ventricle and a right ventricle, said data set comprising frames of said samples acquired over at least one heart cycle;
    obtaining a user input, to the ultrasound system, identifying a measurement feature relative to said at least one heart cycle;
    identifying a reference time within said frames of said data set;
    determining a search interval within said frames of said data set;
    analyzing each said sample in said frames within said search interval to determine a point in time when each said sample reaches said measurement feature;
    determining, for each said sample, a time delay between said reference time and the point in time at which each said sample reaches said measurement feature within said search interval;
    assigning at least one color, from a continuous range of colors, to each said sample based on said time delay for said corresponding individual said sample; and
    displaying a parametric image of said colors assigned to said individual samples for at least one said frame in said search interval to present an amount of synchronization between said samples in said frame.

2. The method of claim 1, further comprising defining said reference time based on a detected QRS.

3. The method of claim 1, further comprising obtaining a user input identifying said search interval.

4. The method of claim 1, further comprising:
    obtaining a second user input identifying a start search time and an end search time defining said search interval; and
    adjusting at least one of said start and end search times based on said second user input.

5. The method of claim 1, wherein said measurement feature represents one of time to peak positive value, time to peak negative value, time to peak absolute value, time to steepest negative-to-positive crossing of a threshold value, time to steepest positive-to-negative crossing of a threshold value, and time to steepest crossing of a threshold value.

6. The method of claim 1, further comprising:
    said obtaining a data set step further comprising storing said data set in a memory; and
    retrieving said data set from said memory prior to processing.

7. The method of claim 1, wherein said measurement feature represents a select state of said samples during said at least one heart cycle.

8. The method of claim 1, further comprising:
    defining a color scale having a range of colors within first and second end points, said at least one color being within said range of colors; and
    associating a smaller said time delay with colors located near said first end point and a larger said time delay with colors located near said second end point.

9. The method of claim 1, further comprising:
    identifying at least one region of interest comprising at least one said sample, said at least one region of interest identifying at least one segment of said left ventricle; and
    said assigning step further comprising assigning a color to said at least one region of interest based on an average of said time delays of said at least one sample.

10. The method of claim 1, further comprising:
    searching said samples within said search interval to locate a time corresponding to said measurement feature; and
    said calculating step further comprising calculating a time delay from said reference time to said time for each said sample.

11. The method of claim 1, further comprising said search interval having start and end search times based on automatically estimated times for start ejection and aortic valve closure, respectively.

12. A method for automatically measuring asynchrony utilizing an ultrasound system, comprising:
    obtaining, from the ultrasound system, a data set of ultrasound samples representative of a left ventricle, said data set comprising frames of said samples acquired over at least one heart cycle;
    identifying a search interval within said frames for each at least one heart cycle based on at least one automatically detected feature within said heart cycle;
    identifying a measurement feature relative to said at least one heart cycle within said search interval;
    analyzing each said sample in said frames within said search interval to determine a point in time when each said sample reaches said measurement feature;
    determining, for each said sample, a time delay between a reference time and the point in time at which each said sample reaches said measurement feature for each said sample within said search interval;
    assigning a color, from a continuous color range, to each said sample based on said time delay for said corresponding individual said sample; and
    displaying a parametric image of said colors assigned to said individual samples for at least one said frame in said search interval to present an amount of synchronization between said samples in said frame.

13. The method of claim 12, further comprising comparing said samples to a predefined range, said predefined range being based on values indicative of normal heart function.

14. The method of claim 12, wherein said measurement feature represents a select state of said samples during said heart cycle.

15. The method of claim 12, further comprising:
said measurement feature further comprising a predefined range being based on values indicative of normal heart function; and
obtaining a user input identifying a second measurement feature different from said first measurement feature, said second measurement feature having a second predefined range different from said predefined range.

16. The method of claim 12, further comprising:
identifying a degree of delay for each said sample; and
defining a color scale with first and second end points having a range of colors, said colors at said first end point representative of a smaller said degree of delay, said colors at said second end point representative of a larger said degree of delay.

17. An ultrasound system for measuring synchronization in moving or deforming tissue, comprising:
a transmitter for transmitting ultrasound signals into an area of interest;
a receiver for receiving echo signals from transmitted ultrasound signals;
a memory for storing a series of image frames comprising said echo signals defining samples, said series of image frames being acquired over at least one heart cycle;
a first user input for inputting a measurement feature, wherein said measurement feature represents a select state of said samples during said at least one heart cycle;
a signal processor identifying a search interval comprising said image frames, said signal processor identifying said measurement feature within said search interval, said signal processor analyzing each said sample in said frames within said search interval to determine a point in time when each said sample reaches said measurement feature, said signal processor identifying time delays from a reference time until points in time at which corresponding said samples reach said measurement feature, said signal processor assigning a color, from a continuous range of colors, to each said sample based on said time delay for said corresponding individual said sample; and
a display displaying a parametric image of said colors assigned to said individual samples for at least one said frame in said search interval to present an amount of synchronization between said samples in said frame.

18. The system of claim 17, further comprising a second user input for inputting at least one of a start time and an end time, said start and end times modifying said search interval.

19. The system of claim 17, further comprising a second user input for changing said search interval, said second user input being one a rotary input, a slider input, a touch screen input, and a soft key input.

20. The system of claim 17, further comprising said first user input being one of a rotary input, a slider input, a touch screen input, and a soft key input.

* * * * *